US007204972B2

(12) United States Patent
Tait et al.

(10) Patent No.: US 7,204,972 B2
(45) Date of Patent: Apr. 17, 2007

(54) ANNEXIN DERIVATIVES WITH ENDOGENOUS CHELATION SITES

(75) Inventors: Jonathan F. Tait, Seattle, WA (US); David S. Brown, Auburn, WA (US)

(73) Assignee: University of Washington, Seattle, WA (US)

( * ) Notice: Subject to any disclaimer, the term of this patent is extended or adjusted under 35 U.S.C. 154(b) by 300 days.

(21) Appl. No.: 11/012,708

(22) Filed: Dec. 15, 2004

(65) Prior Publication Data

US 2005/0095198 A1 May 5, 2005

Related U.S. Application Data

(60) Continuation of application No. 09/970,969, filed on Oct. 3, 2001, now Pat. No. 6,833,448, which is a division of application No. 09/324,096, filed on Jun. 1, 1999, now Pat. No. 6,323,313.

(51) Int. Cl.
*A61K 51/00* (2006.01)
(52) U.S. Cl. .................. 424/1.69; 530/324; 514/12
(58) Field of Classification Search ............. None
See application file for complete search history.

(56) References Cited

U.S. PATENT DOCUMENTS

| 5,591,633 A | 1/1997 | Saino et al. |
| 5,849,261 A | 12/1998 | Dean et al. |
| 5,968,477 A | 10/1999 | Kasina et al. |

FOREIGN PATENT DOCUMENTS

| EP | 0 339 285 A2 | 11/1989 |
| WO | WO 95/19791 A1 | 7/1995 |
| WO | WO 95/34315 A1 | 12/1995 |
| WO | WO 96/17618 A1 | 6/1996 |
| WO | WO 98/04294 A2 | 2/1998 |

OTHER PUBLICATIONS

Blankenberg, F.G., et al., "Imaging of Apoptosis (Programmed Cell Death) with $^{99m}$Tc Annexin V," *The Journal of Nuclear Medicine* 40(1):184-191, Jan. 1999.
Blankenberg, F.G., et al., "*In Vivo* Detection and Imaging of Phosphatidylserine Expression During Programmed Cell Death," *Proceedings of the National Academy of Sciences*. 95:6349-6354, May 1998.
George, A.J.T., et al., "Radiometal Labeling of Recombinant Proteins by a Genetically Engineered Minimal Chelation Site: Technetium-99m Coordination by Single-Chain Fv Antibody Fusion Proteins Through a C-Terminal Cysteinyl Peptide," *Proceedings of the National Academy of Sciences*. 92:8358-8362, Aug. 1995.
Giblin, M.F., et al., "Synthesis and Characterization of Rhenium-Complexed α-Melanotropin Analogs," *Bioconjugate Chem.* 8(3):347-353, 1997.
Huston, J.S., et al., "Single-Chain Fv Radioimmunotargeting," *The Quarterly Journal of Nuclear Medicine* 40(3):320-333, Sep. 1996.
Liberatore, M., et al., "Efficient One-Step Direct Labelling of Recombinant Antibodies with Technetium-99m," *European Journal of Nuclear Medicine* 22(11):1326-1329, Nov. 1995.
Stalteri, M.A., et al., "Comparison of the Stability of Technetium-Labeled Peptides to Challenge with Cysteine," *Bioconjugate Chem.* 10(1):130-136, 1999.
Stratton, J.R., et al., "Selective Uptake of Radiolabeled Annexin V on Acute Porcine Left Atrial Thrombi," *Circulation* 92(10):3113-3121, Nov. 15, 1995.
Vriens, P.W., et al., "The Use of Technetium TC99M Annexin V for In Vivo Imaging of Apoptosis During Cardiac Allograft Rejection," *The Journal of Thoracic and Cardiovascular Surgery* 116(5):844-853, Nov. 1998.

*Primary Examiner*—Sheela J. Huff
(74) *Attorney, Agent, or Firm*—Christensen O'Connor Johnson Kindness PLLC

(57) ABSTRACT

Modified annexins having an N-terminal chelation site comprising an amino acid extension are disclosed. The amino acid extension includes an amino acid sequence $X_1$-Gly-$X_2$, where $X_1$ and $X_2$ are selected from Gly and Cys, where at least one of $X_1$ or $X_2$ is Cys. Radionuclides are readily chelated by the modified annexins to provide radiolabeled annexins useful in imaging vascular thrombi and apoptosis in vivo.

6 Claims, 3 Drawing Sheets

(NH2) Cys-Gly-Gly (CO2H)

(NH2) Gly-Gly-Cys (CO2H)

(NH2) Cys-Gly-Cys (CO2H)

SEQUENCE LISTING

<160> NUMBER OF SEQ ID NOS: 12

<210> SEQ ID NO 1
<211> LENGTH: 981
<212> TYPE: DNA
<213> ORGANISM: Homo sapiens
<220> FEATURE:
<221> NAME/KEY: CDS
<222> LOCATION: (1)..(981)

<400> SEQUENCE: 1

```
atg gca tgt ggt ggc ggc cat atg gca cag gtt ctc aga ggc act gtg    48
Met Ala Cys Gly Gly Gly His Met Ala Gln Val Leu Arg Gly Thr Val
1               5                   10                  15 act gac ttc cct gga ttt gat gag cgg gct gat gca gaa act ctt cgg    96
Thr Asp Phe Pro Gly Phe Asp Glu Arg Ala Asp Ala Glu Thr Leu Arg
                20                  25                  30 aag gct atg aaa ggc ttg ggc aca gat gag gag agc atc ctg act ctg    144
Lys Ala Met Lys Gly Leu Gly Thr Asp Glu Glu Ser Ile Leu Thr Leu
            35                  40                  45 ttg aca tcc cga agt aat gct cag cgc cag gaa atc tct gca gct ttt    192
Leu Thr Ser Arg Ser Asn Ala Gln Arg Gln Glu Ile Ser Ala Ala Phe
        50                  55                  60 aag act ctg ttt ggc agg gat ctt ctg gat gac ctg aaa tca gaa cta    240
Lys Thr Leu Phe Gly Arg Asp Leu Leu Asp Asp Leu Lys Ser Glu Leu
65                  70                  75                  80 act gga aaa ttt gaa aaa tta att gtg gct ctg atg aaa ccc tct cgg    288
Thr Gly Lys Phe Glu Lys Leu Ile Val Ala Leu Met Lys Pro Ser Arg
                85                  90                  95 ctt tat gat gct tat gaa ctg aaa cat gcc ttg aag gga gct gga aca    336
Leu Tyr Asp Ala Tyr Glu Leu Lys His Ala Leu Lys Gly Ala Gly Thr
                100                 105                 110 aat gaa aaa gta ctg aca gaa att att gct tca agg aca cct gaa gaa    384
Asn Glu Lys Val Leu Thr Glu Ile Ile Ala Ser Arg Thr Pro Glu Glu
            115                 120                 125 ctg aga gcc atc aaa caa gtt tat gaa gaa gaa tat ggc tca agc ctg    432
Leu Arg Ala Ile Lys Gln Val Tyr Glu Glu Glu Tyr Gly Ser Ser Leu
        130                 135                 140 gaa gat gac gtg gtg ggg gac act tca ggg tac tac cag cgg atg ttg    480
Glu Asp Asp Val Val Gly Asp Thr Ser Gly Tyr Tyr Gln Arg Met Leu
145                 150                 155                 160 gtg gtt ctc ctt cag gct aac aga gac cct gat gct gga att gat gaa    528
Val Val Leu Leu Gln Ala Asn Arg Asp Pro Asp Ala Gly Ile Asp Glu
                165                 170                 175 gct caa gtt gaa caa gat gct cag gct tta ttt cag gct gga gaa ctt    576
Ala Gln Val Glu Gln Asp Ala Gln Ala Leu Phe Gln Ala Gly Glu Leu
                180                 185                 190 aaa tgg ggg aca gat gaa gaa aag ttt atc acc atc ttt gga aca cga    624
Lys Trp Gly Thr Asp Glu Glu Lys Phe Ile Thr Ile Phe Gly Thr Arg
            195                 200                 205 agt gtg tct cat ttg aga aag gtg ttt gac aag tac atg act ata tca    672
Ser Val Ser His Leu Arg Lys Val Phe Asp Lys Tyr Met Thr Ile Ser
        210                 215                 220 gga ttt caa att gag gaa acc att gac cgc gag act tct ggc aat tta    720
Gly Phe Gln Ile Glu Glu Thr Ile Asp Arg Glu Thr Ser Gly Asn Leu
```

```
                225                 230                 235                 240
gag caa cta ctc ctt gct gtt gtg aaa tct att cga agt ata cct gcc        768
Glu Gln Leu Leu Leu Ala Val Val Lys Ser Ile Arg Ser Ile Pro Ala
                245                 250                 255 tac ctt gca gag acc ctc tat tat gct atg aag gga gct ggg aca gat        816
Tyr Leu Ala Glu Thr Leu Tyr Tyr Ala Met Lys Gly Ala Gly Thr Asp
                260                 265                 270 gat cat acc ctc atc aga gtc atg gtt tcc agg agt gag att gat ctg        864
Asp His Thr Leu Ile Arg Val Met Val Ser Arg Ser Glu Ile Asp Leu
                275                 280                 285 ttt aac atc agg aag gag ttt agg aag aat ttt gcc acc tct ctt tat        912
Phe Asn Ile Arg Lys Glu Phe Arg Lys Asn Phe Ala Thr Ser Leu Tyr
                290                 295                 300 tcc atg att aag gga gat aca tct ggg gac tat aag aaa gct ctt ctg        960
Ser Met Ile Lys Gly Asp Thr Ser Gly Asp Tyr Lys Lys Ala Leu Leu
305                 310                 315                 320 ctg ctc tcc gga gaa gat gac                                            981
Leu Leu Ser Gly Glu Asp Asp
                325

<210> SEQ ID NO 2
<211> LENGTH: 327
<212> TYPE: PRT
<213> ORGANISM: Homo sapiens

<400> SEQUENCE: 2

Met Ala Cys Gly Gly Gly His Met Ala Gln Val Leu Arg Gly Thr Val
1               5                   10                  15

Thr Asp Phe Pro Gly Phe Asp Glu Arg Ala Asp Ala Glu Thr Leu Arg
                20                  25                  30

Lys Ala Met Lys Gly Leu Gly Thr Asp Glu Glu Ser Ile Leu Thr Leu
            35                  40                  45

Leu Thr Ser Arg Ser Asn Ala Gln Arg Gln Glu Ile Ser Ala Ala Phe
        50                  55                  60

Lys Thr Leu Phe Gly Arg Asp Leu Leu Asp Asp Leu Lys Ser Glu Leu
65                  70                  75                  80

Thr Gly Lys Phe Glu Lys Leu Ile Val Ala Leu Met Lys Pro Ser Arg
                85                  90                  95

Leu Tyr Asp Ala Tyr Glu Leu Lys His Ala Leu Lys Gly Ala Gly Thr
            100                 105                 110

Asn Glu Lys Val Leu Thr Glu Ile Ile Ala Ser Arg Thr Pro Glu Glu
        115                 120                 125

Leu Arg Ala Ile Lys Gln Val Tyr Glu Glu Tyr Gly Ser Ser Leu
130                 135                 140

Glu Asp Asp Val Val Gly Asp Thr Ser Gly Tyr Tyr Gln Arg Met Leu
145                 150                 155                 160

Val Val Leu Leu Gln Ala Asn Arg Asp Pro Asp Ala Gly Ile Asp Glu
                165                 170                 175

Ala Gln Val Glu Gln Asp Ala Gln Ala Leu Phe Gln Ala Gly Glu Leu
            180                 185                 190

Lys Trp Gly Thr Asp Glu Glu Lys Phe Ile Thr Ile Phe Gly Thr Arg
        195                 200                 205

Ser Val Ser His Leu Arg Lys Val Phe Asp Lys Tyr Met Thr Ile Ser
    210                 215                 220

Gly Phe Gln Ile Glu Glu Thr Ile Asp Arg Glu Thr Ser Gly Asn Leu
225                 230                 235                 240
```

```
Glu Gln Leu Leu Leu Ala Val Val Lys Ser Ile Arg Ser Ile Pro Ala
                245                 250                 255

Tyr Leu Ala Glu Thr Leu Tyr Tyr Ala Met Lys Gly Ala Gly Thr Asp
            260                 265                 270

Asp His Thr Leu Ile Arg Val Met Val Ser Arg Ser Glu Ile Asp Leu
        275                 280                 285

Phe Asn Ile Arg Lys Glu Phe Arg Lys Asn Phe Ala Thr Ser Leu Tyr
    290                 295                 300

Ser Met Ile Lys Gly Asp Thr Ser Gly Asp Tyr Lys Lys Ala Leu Leu
305                 310                 315                 320

Leu Leu Ser Gly Glu Asp Asp
                325

<210> SEQ ID NO 3
<211> LENGTH: 981
<212> TYPE: DNA
<213> ORGANISM: Homo sapiens
<220> FEATURE:
<221> NAME/KEY: CDS
<222> LOCATION: (1)..(981)

<400> SEQUENCE: 3
```

| | | | | | | | | | | | | | | | | |
|---|---|---|---|---|---|---|---|---|---|---|---|---|---|---|---|---|
| atg | gca | ggt | ggc | tgt | ggc | cat | atg | gca | cag | gtt | ctc | aga | ggc | act | gtg | 48 |
| Met | Ala | Gly | Gly | Cys | Gly | His | Met | Ala | Gln | Val | Leu | Arg | Gly | Thr | Val | |
| 1 | | | | 5 | | | | | 10 | | | | | 15 | | |
| act | gac | ttc | cct | gga | ttt | gat | gag | cgg | gct | gat | gca | gaa | act | ctt | cgg | 96 |
| Thr | Asp | Phe | Pro | Gly | Phe | Asp | Glu | Arg | Ala | Asp | Ala | Glu | Thr | Leu | Arg | |
| | | | 20 | | | | | 25 | | | | | 30 | | | |
| aag | gct | atg | aaa | ggc | ttg | ggc | aca | gat | gag | gag | agc | atc | ctg | act | ctg | 144 |
| Lys | Ala | Met | Lys | Gly | Leu | Gly | Thr | Asp | Glu | Glu | Ser | Ile | Leu | Thr | Leu | |
| | | | | 35 | | | | | 40 | | | | | 45 | | |
| ttg | aca | tcc | cga | agt | aat | gct | cag | cgc | cag | gaa | atc | tct | gca | gct | ttt | 192 |
| Leu | Thr | Ser | Arg | Ser | Asn | Ala | Gln | Arg | Gln | Glu | Ile | Ser | Ala | Ala | Phe | |
| | | 50 | | | | | 55 | | | | | 60 | | | | |
| aag | act | ctg | ttt | ggc | agg | gat | ctt | ctg | gat | gac | ctg | aaa | tca | gaa | cta | 240 |
| Lys | Thr | Leu | Phe | Gly | Arg | Asp | Leu | Leu | Asp | Asp | Leu | Lys | Ser | Glu | Leu | |
| 65 | | | | | 70 | | | | | 75 | | | | | 80 | |
| act | gga | aaa | ttt | gaa | aaa | tta | att | gtg | gct | ctg | atg | aaa | ccc | tct | cgg | 288 |
| Thr | Gly | Lys | Phe | Glu | Lys | Leu | Ile | Val | Ala | Leu | Met | Lys | Pro | Ser | Arg | |
| | | | | 85 | | | | | 90 | | | | | 95 | | |
| ctt | tat | gat | gct | tat | gaa | ctg | aaa | cat | gcc | ttg | aag | gga | gct | gga | aca | 336 |
| Leu | Tyr | Asp | Ala | Tyr | Glu | Leu | Lys | His | Ala | Leu | Lys | Gly | Ala | Gly | Thr | |
| | | | 100 | | | | | 105 | | | | | 110 | | | |
| aat | gaa | aaa | gta | ctg | aca | gaa | att | att | gct | tca | agg | aca | cct | gaa | gaa | 384 |
| Asn | Glu | Lys | Val | Leu | Thr | Glu | Ile | Ile | Ala | Ser | Arg | Thr | Pro | Glu | Glu | |
| | | | | 115 | | | | | 120 | | | | | 125 | | |
| ctg | aga | gcc | atc | aaa | caa | gtt | tat | gaa | gaa | gaa | tat | ggc | tca | agc | ctg | 432 |
| Leu | Arg | Ala | Ile | Lys | Gln | Val | Tyr | Glu | Glu | Glu | Tyr | Gly | Ser | Ser | Leu | |
| | | 130 | | | | | 135 | | | | | 140 | | | | |
| gaa | gat | gac | gtg | gtg | ggg | gac | act | tca | ggg | tac | tac | cag | cgg | atg | ttg | 480 |
| Glu | Asp | Asp | Val | Val | Gly | Asp | Thr | Ser | Gly | Tyr | Tyr | Gln | Arg | Met | Leu | |
| 145 | | | | | 150 | | | | | 155 | | | | | 160 | |
| gtg | gtt | ctc | ctt | cag | gct | aac | aga | gac | cct | gat | gct | gga | att | gat | gaa | 528 |
| Val | Val | Leu | Leu | Gln | Ala | Asn | Arg | Asp | Pro | Asp | Ala | Gly | Ile | Asp | Glu | |
| | | | | 165 | | | | | 170 | | | | | 175 | | |
| gct | caa | gtt | gaa | caa | gat | gct | cag | gct | tta | ttt | cag | gct | gga | gaa | ctt | 576 |
| Ala | Gln | Val | Glu | Gln | Asp | Ala | Gln | Ala | Leu | Phe | Gln | Ala | Gly | Glu | Leu | |
| | | | 180 | | | | | 185 | | | | | 190 | | | |
| aaa | tgg | ggg | aca | gat | gaa | gaa | aag | ttt | atc | acc | atc | ttt | gga | aca | cga | 624 |
| Lys | Trp | Gly | Thr | Asp | Glu | Glu | Lys | Phe | Ile | Thr | Ile | Phe | Gly | Thr | Arg | |

-continued

```
                195                 200                 205
agt gtg tct cat ttg aga aag gtg ttt gac aag tac atg act ata tca    672
Ser Val Ser His Leu Arg Lys Val Phe Asp Lys Tyr Met Thr Ile Ser
    210                 215                 220 gga ttt caa att gag gaa acc att gac cgc gag act tct ggc aat tta    720
Gly Phe Gln Ile Glu Glu Thr Ile Asp Arg Glu Thr Ser Gly Asn Leu
225                 230                 235                 240 gag caa cta ctc ctt gct gtt gtg aaa tct att cga agt ata cct gcc    768
Glu Gln Leu Leu Leu Ala Val Val Lys Ser Ile Arg Ser Ile Pro Ala
        245                 250                 255 tac ctt gca gag acc ctc tat tat gct atg aag gga gct ggg aca gat    816
Tyr Leu Ala Glu Thr Leu Tyr Tyr Ala Met Lys Gly Ala Gly Thr Asp
            260                 265                 270 gat cat acc ctc atc aga gtc atg gtt tcc agg agt gag att gat ctg    864
Asp His Thr Leu Ile Arg Val Met Val Ser Arg Ser Glu Ile Asp Leu
                275                 280                 285 ttt aac atc agg aag gag ttt agg aag aat ttt gcc acc tct ctt tat    912
Phe Asn Ile Arg Lys Glu Phe Arg Lys Asn Phe Ala Thr Ser Leu Tyr
            290                 295                 300 tcc atg att aag gga gat aca tct ggg gac tat aag aaa gct ctt ctg    960
Ser Met Ile Lys Gly Asp Thr Ser Gly Asp Tyr Lys Lys Ala Leu Leu
305                 310                 315                 320 ctg ctc tcc gga gaa gat gac                                        981
Leu Leu Ser Gly Glu Asp Asp
                325
```

<210> SEQ ID NO 4
<211> LENGTH: 327
<212> TYPE: PRT
<213> ORGANISM: Homo sapiens

<400> SEQUENCE: 4

```
Met Ala Gly Gly Cys Gly His Met Ala Gln Val Leu Arg Gly Thr Val
1               5                   10                  15

Thr Asp Phe Pro Gly Phe Asp Glu Arg Ala Asp Ala Glu Thr Leu Arg
            20                  25                  30

Lys Ala Met Lys Gly Leu Gly Thr Asp Glu Glu Ser Ile Leu Thr Leu
        35                  40                  45

Leu Thr Ser Arg Ser Asn Ala Gln Arg Gln Glu Ile Ser Ala Ala Phe
    50                  55                  60

Lys Thr Leu Phe Gly Arg Asp Leu Leu Asp Asp Leu Lys Ser Glu Leu
65                  70                  75                  80

Thr Gly Lys Phe Glu Lys Leu Ile Val Ala Leu Met Lys Pro Ser Arg
                85                  90                  95

Leu Tyr Asp Ala Tyr Glu Leu Lys His Ala Leu Lys Gly Ala Gly Thr
            100                 105                 110

Asn Glu Lys Val Leu Thr Glu Ile Ile Ala Ser Arg Thr Pro Glu Glu
        115                 120                 125

Leu Arg Ala Ile Lys Gln Val Tyr Glu Glu Tyr Gly Ser Ser Leu
    130                 135                 140

Glu Asp Asp Val Val Gly Asp Thr Ser Gly Tyr Tyr Gln Arg Met Leu
145                 150                 155                 160

Val Val Leu Leu Gln Ala Asn Arg Asp Pro Asp Ala Gly Ile Asp Glu
                165                 170                 175

Ala Gln Val Glu Gln Asp Ala Gln Ala Leu Phe Gln Ala Gly Glu Leu
            180                 185                 190

Lys Trp Gly Thr Asp Glu Glu Lys Phe Ile Thr Ile Phe Gly Thr Arg
```

```
            195                 200                 205
Ser Val Ser His Leu Arg Lys Val Phe Asp Lys Tyr Met Thr Ile Ser
    210                 215                 220

Gly Phe Gln Ile Glu Glu Thr Ile Asp Arg Glu Thr Ser Gly Asn Leu
225                 230                 235                 240

Glu Gln Leu Leu Leu Ala Val Val Lys Ser Ile Arg Ser Ile Pro Ala
            245                 250                 255

Tyr Leu Ala Glu Thr Leu Tyr Tyr Ala Met Lys Gly Ala Gly Thr Asp
            260                 265                 270

Asp His Thr Leu Ile Arg Val Met Val Ser Arg Ser Glu Ile Asp Leu
            275                 280                 285

Phe Asn Ile Arg Lys Glu Phe Arg Lys Asn Phe Ala Thr Ser Leu Tyr
            290                 295                 300

Ser Met Ile Lys Gly Asp Thr Ser Gly Asp Tyr Lys Lys Ala Leu Leu
305                 310                 315                 320

Leu Leu Ser Gly Glu Asp Asp
            325

<210> SEQ ID NO 5
<211> LENGTH: 981
<212> TYPE: DNA
<213> ORGANISM: Homo sapiens
<220> FEATURE:
<221> NAME/KEY: CDS
<222> LOCATION: (1)..(981)

<400> SEQUENCE: 5 atg gca tgt ggc tgc ggt cat atg gca cag gtt ctc aga ggc act gtg      48
Met Ala Cys Gly Cys Gly His Met Ala Gln Val Leu Arg Gly Thr Val
1               5                   10                  15 act gac ttc cct gga ttt gat gag cgg gct gat gca gaa act ctt cgg      96
Thr Asp Phe Pro Gly Phe Asp Glu Arg Ala Asp Ala Glu Thr Leu Arg
                20                  25                  30 aag gct atg aaa ggc ttg ggc aca gat gag gag agc atc ctg act ctg     144
Lys Ala Met Lys Gly Leu Gly Thr Asp Glu Glu Ser Ile Leu Thr Leu
            35                  40                  45 ttg aca tcc cga agt aat gct cag cgc cag gaa atc tct gca gct ttt     192
Leu Thr Ser Arg Ser Asn Ala Gln Arg Gln Glu Ile Ser Ala Ala Phe
        50                  55                  60 aag act ctg ttt ggc agg gat ctt ctg gat gac ctg aaa tca gaa cta     240
Lys Thr Leu Phe Gly Arg Asp Leu Leu Asp Asp Leu Lys Ser Glu Leu
65                  70                  75                  80 act gga aaa ttt gaa aaa tta att gtg gct ctg atg aaa ccc tct cgg     288
Thr Gly Lys Phe Glu Lys Leu Ile Val Ala Leu Met Lys Pro Ser Arg
                85                  90                  95 ctt tat gat gct tat gaa ctg aaa cat gcc ttg aag gga gct gga aca     336
Leu Tyr Asp Ala Tyr Glu Leu Lys His Ala Leu Lys Gly Ala Gly Thr
                100                 105                 110 aat gaa aaa gta ctg aca gaa att att gct tca agg aca cct gaa gaa     384
Asn Glu Lys Val Leu Thr Glu Ile Ile Ala Ser Arg Thr Pro Glu Glu
            115                 120                 125 ctg aga gcc atc aaa caa gtt tat gaa gaa gaa tat ggc tca agc ctg     432
Leu Arg Ala Ile Lys Gln Val Tyr Glu Glu Glu Tyr Gly Ser Ser Leu
        130                 135                 140 gaa gat gac gtg gtg ggg gac act tca ggg tac tac cag cgg atg ttg     480
Glu Asp Asp Val Val Gly Asp Thr Ser Gly Tyr Tyr Gln Arg Met Leu
145                 150                 155                 160 gtg gtt ctc ctt cag gct aac aga gac cct gat gct gga att gat gaa     528
Val Val Leu Leu Gln Ala Asn Arg Asp Pro Asp Ala Gly Ile Asp Glu
```

```
                165                 170                 175
gct caa gtt gaa caa gat gct cag gct tta ttt cag gct gga gaa ctt      576
Ala Gln Val Glu Gln Asp Ala Gln Ala Leu Phe Gln Ala Gly Glu Leu
            180                 185                 190 aaa tgg ggg aca gat gaa gaa aag ttt atc acc atc ttt gga aca cga      624
Lys Trp Gly Thr Asp Glu Glu Lys Phe Ile Thr Ile Phe Gly Thr Arg
        195                 200                 205 agt gtg tct cat ttg aga aag gtg ttt gac aag tac atg act ata tca      672
Ser Val Ser His Leu Arg Lys Val Phe Asp Lys Tyr Met Thr Ile Ser
    210                 215                 220 gga ttt caa att gag gaa acc att gac cgc gag act tct ggc aat tta      720
Gly Phe Gln Ile Glu Glu Thr Ile Asp Arg Glu Thr Ser Gly Asn Leu
225                 230                 235                 240 gag caa cta ctc ctt gct gtt gtg aaa tct att cga agt ata cct gcc      768
Glu Gln Leu Leu Leu Ala Val Val Lys Ser Ile Arg Ser Ile Pro Ala
                245                 250                 255 tac ctt gca gag acc ctc tat tat gct atg aag gga gct ggg aca gat      816
Tyr Leu Ala Glu Thr Leu Tyr Tyr Ala Met Lys Gly Ala Gly Thr Asp
            260                 265                 270 gat cat acc ctc atc aga gtc atg gtt tcc agg agt gag att gat ctg      864
Asp His Thr Leu Ile Arg Val Met Val Ser Arg Ser Glu Ile Asp Leu
        275                 280                 285 ttt aac atc agg aag gag ttt agg aag aat ttt gcc acc tct ctt tat      912
Phe Asn Ile Arg Lys Glu Phe Arg Lys Asn Phe Ala Thr Ser Leu Tyr
    290                 295                 300 tcc atg att aag gga gat aca tct ggg gac tat aag aaa gct ctt ctg      960
Ser Met Ile Lys Gly Asp Thr Ser Gly Asp Tyr Lys Lys Ala Leu Leu
305                 310                 315                 320 ctg ctc tcc gga gaa gat gac                                          981
Leu Leu Ser Gly Glu Asp Asp
                325

<210> SEQ ID NO 6
<211> LENGTH: 327
<212> TYPE: PRT
<213> ORGANISM: Homo sapiens

<400> SEQUENCE: 6

Met Ala Cys Gly Cys Gly His Met Ala Gln Val Leu Arg Gly Thr Val
1               5                   10                  15

Thr Asp Phe Pro Gly Phe Asp Glu Arg Ala Asp Ala Glu Thr Leu Arg
            20                  25                  30

Lys Ala Met Lys Gly Leu Gly Thr Asp Glu Glu Ser Ile Leu Thr Leu
        35                  40                  45

Leu Thr Ser Arg Ser Asn Ala Gln Arg Gln Glu Ile Ser Ala Ala Phe
    50                  55                  60

Lys Thr Leu Phe Gly Arg Asp Leu Leu Asp Asp Leu Lys Ser Glu Leu
65                  70                  75                  80

Thr Gly Lys Phe Glu Lys Leu Ile Val Ala Leu Met Lys Pro Ser Arg
                85                  90                  95

Leu Tyr Asp Ala Tyr Glu Leu Lys His Ala Leu Lys Gly Ala Gly Thr
            100                 105                 110

Asn Glu Lys Val Leu Thr Glu Ile Ile Ala Ser Arg Thr Pro Glu Glu
        115                 120                 125

Leu Arg Ala Ile Lys Gln Val Tyr Glu Glu Glu Tyr Gly Ser Ser Leu
    130                 135                 140

Glu Asp Asp Val Val Gly Asp Thr Ser Gly Tyr Tyr Gln Arg Met Leu
145                 150                 155                 160
```

```
Val Val Leu Leu Gln Ala Asn Arg Asp Pro Asp Ala Gly Ile Asp Glu
                165                 170                 175
Ala Gln Val Glu Gln Asp Ala Gln Ala Leu Phe Gln Ala Gly Glu Leu
            180                 185                 190
Lys Trp Gly Thr Asp Glu Glu Lys Phe Ile Thr Ile Phe Gly Thr Arg
        195                 200                 205
Ser Val Ser His Leu Arg Lys Val Phe Asp Lys Tyr Met Thr Ile Ser
    210                 215                 220
Gly Phe Gln Ile Glu Glu Thr Ile Asp Arg Glu Thr Ser Gly Asn Leu
225                 230                 235                 240
Glu Gln Leu Leu Leu Ala Val Val Lys Ser Ile Arg Ser Ile Pro Ala
                245                 250                 255
Tyr Leu Ala Glu Thr Leu Tyr Tyr Ala Met Lys Gly Ala Gly Thr Asp
            260                 265                 270
Asp His Thr Leu Ile Arg Val Met Val Ser Arg Ser Glu Ile Asp Leu
        275                 280                 285
Phe Asn Ile Arg Lys Glu Phe Arg Lys Asn Phe Ala Thr Ser Leu Tyr
    290                 295                 300
Ser Met Ile Lys Gly Asp Thr Ser Gly Asp Tyr Lys Lys Ala Leu Leu
305                 310                 315                 320
Leu Leu Ser Gly Glu Asp Asp
                325

<210> SEQ ID NO 7
<211> LENGTH: 21
<212> TYPE: DNA
<213> ORGANISM: Homo sapiens

<400> SEQUENCE: 7
tatggcatgt ggcggtggcc a                                         21

<210> SEQ ID NO 8
<211> LENGTH: 21
<212> TYPE: DNA
<213> ORGANISM: Homo sapiens

<400> SEQUENCE: 8
tatggccacc gccacatgcc a                                         21

<210> SEQ ID NO 9
<211> LENGTH: 21
<212> TYPE: DNA
<213> ORGANISM: Homo sapiens

<400> SEQUENCE: 9
tatggcaggt ggctgtggcc a                                         21

<210> SEQ ID NO 10
<211> LENGTH: 21
<212> TYPE: DNA
<213> ORGANISM: Homo sapiens

<400> SEQUENCE: 10
tatggccaca gccacctgcc a                                         21

<210> SEQ ID NO 11
<211> LENGTH: 21
<212> TYPE: DNA
<213> ORGANISM: Homo sapiens
```

```
<400> SEQUENCE: 11
tatggcatgt ggctgcggtc a                                              21

<210> SEQ ID NO 12
<211> LENGTH: 21
<212> TYPE: DNA
<213> ORGANISM: Homo sapiens

<400> SEQUENCE: 12
tatgaccgca gccacatgcc a                                              21
```

ANNEXIN DERIVATIVES WITH ENDOGENOUS CHELATION SITES

CROSS-REFERENCES TO RELATED APPLICATIONS

This application is a continuation of U.S. patent application Ser. No. 09/970,969, dated Oct. 3, 2001 now U.S. Pat. No. 6,833,448, which is a divisional of U.S. patent application Ser. No. 09/324,096, filed Jun. 1, 1999, now U.S. Pat. No. 6,323,313 B1, issued Nov. 27, 2001, the benefit of the priority of the filing dates of which are hereby claimed under 35 U.S.C. § 120.

FIELD OF THE INVENTION

The present invention relates to annexin derivatives having chelation sites, radiolabeled annexin derivatives, and imaging methods using radiolabeled annexin derivatives.

BACKGROUND OF THE INVENTION

The formation of vascular thrombi is a significant complicating factor for atherosclerosis and coronary trauma or disease. Techniques for determining the presence of vascular thrombi include invasive techniques that are often cumbersome and fail to detect thrombi with good sensitivity and specificity. Available non-invasive techniques are often of limited value and fail to image arterial thrombi. Common arterial thrombosis imaging use radionuclide methods that are complex and time consuming, and limited in their practical utility. More importantly, these methods generally fail to detect small thrombi which are of significant clinical importance, particularly in coronary arterial thrombi.

Activated platelets associated with vascular thrombi, express phosphatidylserine, an anionic phospholipid, in an amount significantly greater than quiescent platelets, which express little, if any, phosphatidylserine. Annexins are a class of proteins that are characterized by calcium-mediated binding to anionic phospholipids. Annexin V is a human protein of 319 amino acids with a molecular weight of 36,000 Daltons and binds to phosphatidylserine with a high affinity ($K_d$=7 nM/L). Accordingly, annexin V offers the potential for selective targeting of platelet thrombi. Furthermore, because there is virtually no circulating annexin V endogenous pool to compete for binding sites on thrombi or to dilute exogenously administered annexin V, annexin V is an attractive candidate for the non-invasive detection of vascular thrombi. Recently, radiolabeled annexins derivatives have been used to image vascular thrombi in vivo. Stratton et al., *Circulation*, 92:3113–3121, 1995.

In addition to its association with vascular thrombi, cell surface expression of phosphatidylserine also occurs during apoptosis. One of the earliest events in programmed cell death is the externalization of phosphatidylserine, a membrane phospholipid normally restricted to the inner leaflet of the lipid bilayer. Cells undergoing apoptosis redistribute phosphatidylserine from the inner leaflet of the plasma membrane lipid bilayer to the outer leaflet.

Cell death can occur either through necrosis, which results in uncontrolled release of a variety of intracellular substances, or through apoptosis, which is an orchestrated sequence leaving little cellular residue. Through apoptosis, cellular debris is absorbed by neighboring cells without damage to adjacent tissue or extracellular matrix. Apoptosis (or programmed cell death) plays an important role in a number of physiological events including embryogenesis, regulation of the immune system, and homeostasis. Programmed cell death also plays a role in the pathogenesis of a number of disorders including AIDS and other viral illnesses, cerebral and myocardio ischemia, autoimmune and neurodegenerative diseases, organ and bone marrow transplant rejection, and tumor response to chemotherapy and radiation.

Apoptosis has been determined in histological sections with in situ staining of DNA breaks, formed by the cleavage of chromatin by endonucleases, by terminal deoxynucleotidyl-transferase-mediated deoxyuridine triphosphate-biotin nick-and labeling imaging.

Because annexin has a high affinity for cell membranes expressing phosphatidylserine, annexin V derivatives have been utilized to detect apoptosis in hematopoietic cells, neurons, fibroblasts, endothelial cells, smooth muscle cells, carcinomas, lymphomas, all murine embryonic cell types and plant and insect cells. The utility of a radiolabeled annexin V for in vivo imaging of phosphatidylserine expression associated with apoptosis has been reported. Blankenberg et al., *Proc. Natl. Acad. Sci. U.S.A.*, 95:6349–6354, 1998. In the report, phosphatidylserine expression during programmed cell death was detected and imaged through the use of a radiolabeled annexin conjugate ($^{99m}$Tc HYNIC-annexin V). The use of the same radiolabeled annexin conjugate for in vivo imaging of apoptosis during cardiac allograft rejection has also been reported. Vriens et al., *The Journal of Thoracic and Cardiovascular Surgery*, 116:844–853, 1998.

Despite the benefits and advantages related to the annexin-based imaging agents noted above, a need for improved annexin-based imaging agents that are effective as imaging vascular thrombi and apoptosis and more readily prepared than the currently used annexin conjugates. The present invention seeks to fulfill these needs and provides further related advantages.

SUMMARY OF THE INVENTION

In one aspect, the present invention provides a modified annexin having an N-terminal chelation site. By virtue of the chelation site, the modified annexin readily chelates a radionuclide to provide a radiolabeled annexin. In a preferred embodiment, the modified annexin includes an endogenous chelation site that is formed recombinantly. Methods for forming the modified annexin and radiolabeled annexin are also provided.

In another aspect of the present invention, a method for imaging vascular thrombi is provided. In the method, vascular thrombi are imaged using a modified annexin having an N-terminal chelation site to which is complexed a radionuclide.

In a further aspect, the present invention provides a method for imaging apoptosis. In the method, apoptosis is imaged using a modified annexin having an N-terminal chelation site to which is complexed a radionuclide.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 1A–1C are chemical structures for the chelation sites of the invention shown with chelated technetium.

DETAILED DESCRIPTION OF THE PREFERRED EMBODIMENT

The present invention relates to annexin derivatives. As used herein, the term "annexin" refers to a class of proteins characterized by their ability to bind with high affinity to membrane lipids in the presence of millimolar concentrations of calcium. Annexins have been shown to exhibit anticoagulatory effects that are mediated by the binding of annexins to negatively charged surface phospholipids (e.g., on activated platelets). Annexin V is a representative annexin molecule used in the description of the present invention. Annexins within the scope of the invention include annexins I, II, III, IV, V, VI, VII, VIII, XI, XIII, XXXI, and XXXII. The term "annexin" includes native annexin purified from natural sources such as, for example, human placenta, or annexin molecules containing a native sequence produced through genetic engineering, recombinant, or other means. The term "annexin" includes modified annexins as defined below, derived from or produced by any source. As used herein, the term "modified annexin" refers to an annexin molecule wherein the native sequence or molecule is altered in such a way without materially altering the membrane binding affinity of the annexin. Such annexins can be produced by chemical, genetic engineering, or recombinant techniques. The modification can include sequence modification through the addition of several amino acid residues, and/or an addition/deletion of an amino acid at a single site on the native or genetically engineered sequence. In the context of the present invention, modified annexins include annexins modified at the N-terminus by the addition of amino acid residues.

In one aspect, the present invention provides a modified annexin suitable for radiolabeling with a diagnostic imaging agent. In a preferred embodiment, the present invention provides a modified annexin having an N-terminal chelation site comprising an amino acid extension. The amino acid extension includes an amino acid sequence having at least one glycine and at least one cysteine in the amino acid sequence. In a preferred embodiment, the amino acid extension has an amino acid sequence $X_1$-Gly-$X_2$, where $X_1$ and $X_2$ are selected from Gly and Cys, where at least one of $X_1$ or $X_2$ is Cys. Accordingly, preferred amino acid extension include the amino acid sequences: Gly-Gly-Cys, Cys-Gly-Gly, and Cys-Gly-Cys.

The amino acid extension can further include one or more amino acids at either terminus of the extension. The nature of these additional amino acids is not particularly critical provided that the additional amino acids do not affect either annexin binding required for imaging or the ability of the modified annexin to chelate a radionuclide. For example, the sequences noted above can be preceded by an amino acid such as histidine and/or glycine and followed by an amino acid such as alanine.

Figure 1A:
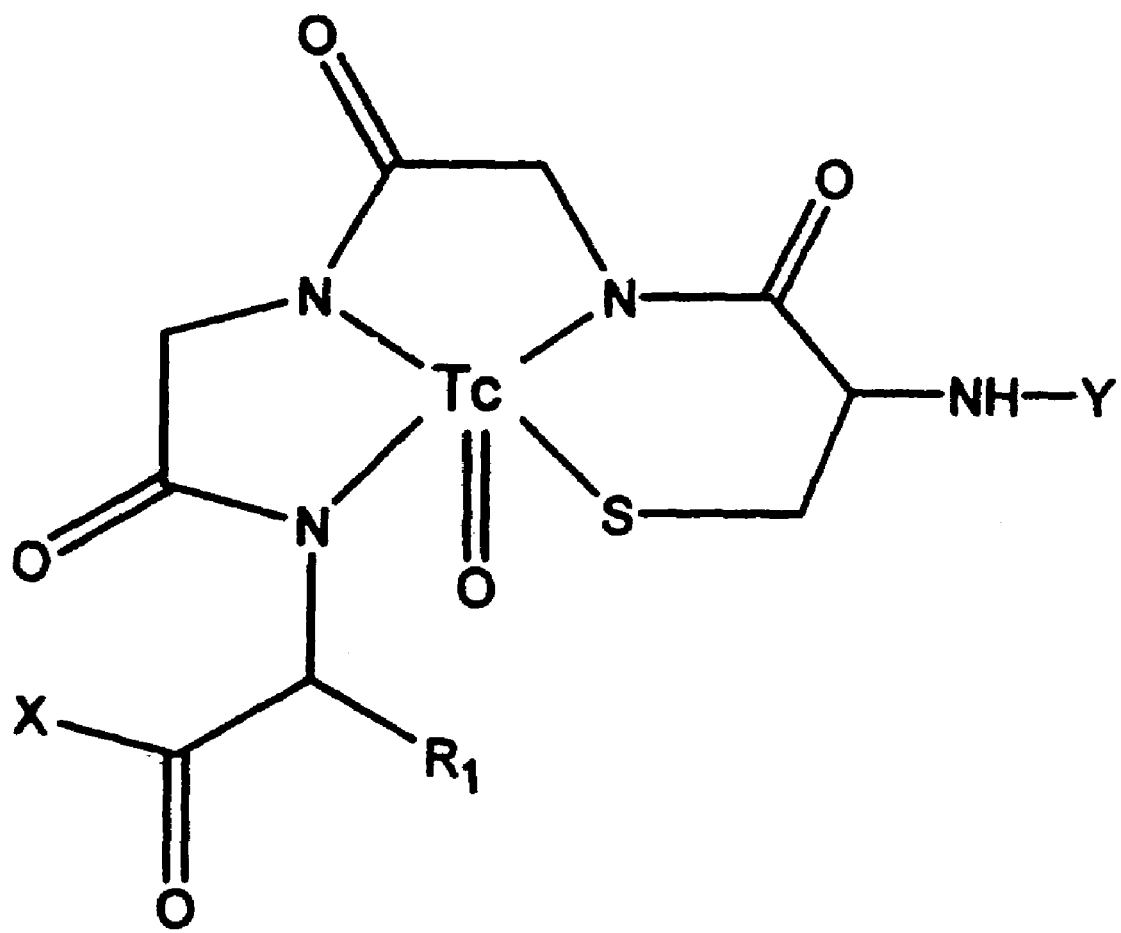
Figure 1B:
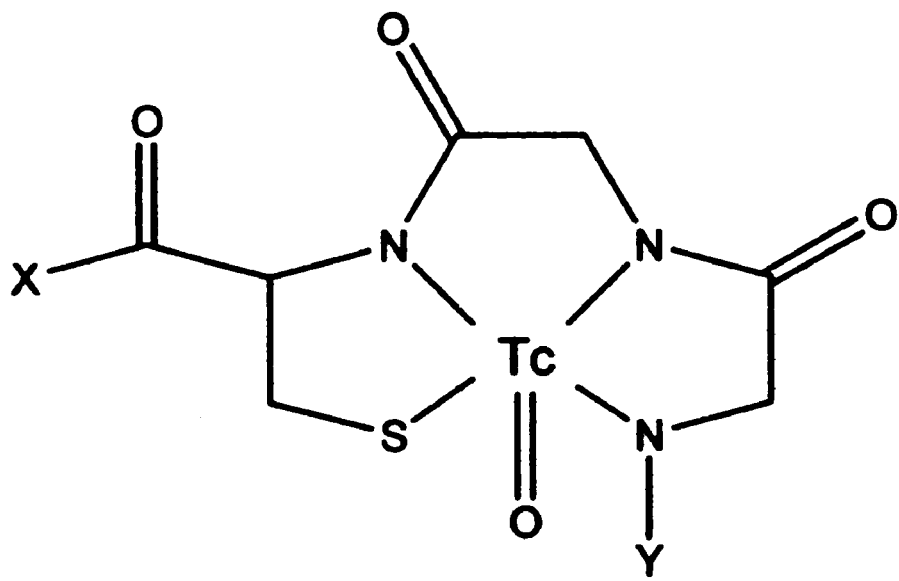
Figure 1C:
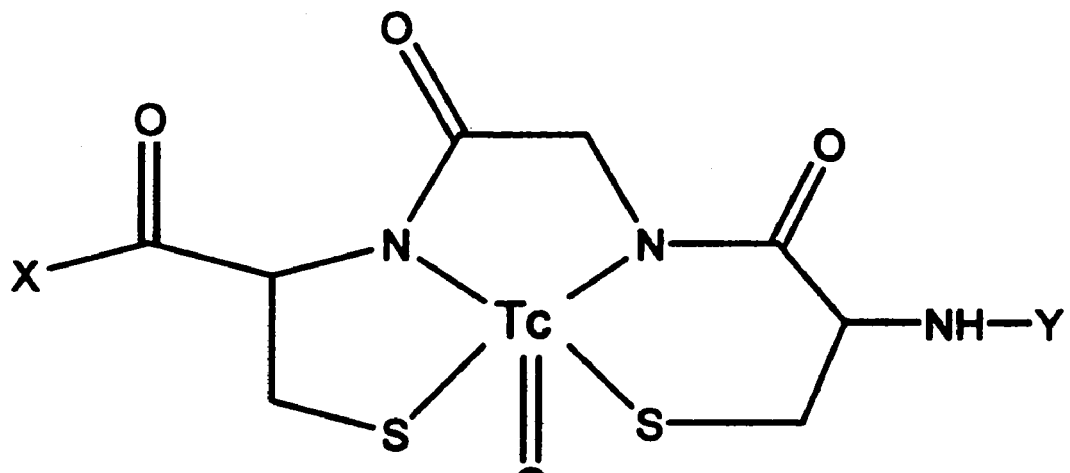

The proposed structures for the amino acid extensions with chelated technetium are illustrated in FIG. 1. FIGS. 1A–1C depict chemical structures for the chelation sites corresponding to the amino acid sequences Cys-Gly-Gly, Gly-Gly-Cys, and Cys-Gly-Cys, respectively. In these figures, "X" and "Y" refer to the portions of a molecule (e.g., one or more additional amino acids) beyond the chelation site. Alternatively, "X" can represent the C-terminal and "Y" can represent the N-terminal of a molecule including the chelation site. For example, "X" can represent the sequence of amino acids leading to a polypeptide's C-terminal (e.g., annexin C-terminal) and "Y" can represent the sequence of amino acids leading to a polypeptide's N-terminal (e.g., modified annexin N-terminal). Referring to FIG. 1A, technetium is chelated by nitrogen and sulfur atoms from the amino acid sequence Cys-Gly-Gly as shown. The figure shows that chelation includes a nitrogen atom from the amide bond of an adjacent amino acid ($R_1$ is an amino acid substituent selected from among the substituents for naturally occurring amino acids).

The chelation site including one of the amino acid sequences noted above is located at the N-terminus of the annexin molecule. Annexin's N-terminus is remote from its biological binding site. A representative modified annexin having an amino acid sequence including the extension Cys-Gly-Gly is set forth in SEQ ID NO:2. A modified annexin having the amino acid sequence including the extension Gly-Gly-Cys is set forth in SEQ ID NO:4 A representative modified annexin having an amino acid sequence including the extension Cys-Gly-Cys is set forth in SEQ ID NO:6. The modified annexins having the amino acid sequences set forth in SEQ ID NO:2, SEQ ID NO:4, and SEQ ID NO:6 include their N-terminal methionine residues, which are normally removed post-translationally in both humans and E. coli. In preferred embodiments, the modified annexin is mutated to include serine at position 316. Such a modification results in the substitution of serine for cysteine.

The modified annexins of the present invention include an N-terminal amino acid extension. The amino acid extension can be added to the annexin through chemical means. Alternatively, in a preferred embodiment, the amino acid extension is genetically engineered (i.e., incorporated into the annexin by recombinant techniques). Accordingly, the modified annexins of the invention are preferably prepared by genetic engineering. Briefly, a cDNA encoding a wild-type or mutant annexin V was cloned into a vector (e.g., pET12a) and then transformed into an E. coli strain (e.g., BL21(DE3)). The cell line was then grown in growth media and the expressed protein was harvested and purified. A representative method for preparing the modified annexins of the present invention is described in Examples 1 and 2. By this method, the present invention provides bioengineered forms of annexin V having endogenous chelation sites.

In another embodiment, the present invention provides an isolated nucleic acid molecule encoding the modified annexins noted above. The present invention provides isolated nucleic acid molecules encoding modified annexins having the amino acid sequences set forth in SEQ ID NO:2, SEQ ID NO:4, and SEQ ID NO:6. More specifically, the present invention provides isolated nucleic acid molecules having the nucleic acid sequences set forth in SEQ ID NO:1, SEQ ID NO:3, and SEQ ID NO:5.

The present invention also provides a replicable expression vector comprising a nucleic acid sequence encoding a modified annexin as described above. The invention provides a replicable expression vector comprising a nucleic acid sequence encoding a modified annexin having an N-terminal chelation site that includes an amino acid sequence $X_1$-Gly-$X_2$, where $X_1$ and $X_2$ are selected from Gly and Cys, and where at least one of $X_1$ or $X_2$ is Cys. The present invention also provides replicable expression vectors comprising nucleic acid sequences encoding modified annexins having the amino acid sequences set forth in SEQ ID NO:2, SEQ ID NO:4, and SEQ ID NO:6.

The modified annexins of the present invention are preferably purified recombinant proteins harvested from host cells incorporating expression vectors that encode the modified annexins. Thus, in another aspect, the present invention provides host cells comprising expression vectors encoding the modified annexins of the present invention. The present invention provides host cells including an expression vector comprising a nucleic acid sequence encoding a modified annexin having an N-terminal chelation site including an amino acid sequence $X_1$-Gly-$X_2$, where $X_1$ and $X_2$ are selected from Gly and Cys, and where at least of $X_1$ or $X_2$ is Cys. The present invention also provides host cells including expression vectors having nucleic acid sequences encoding the modified annexins having the amino acid sequences set forth in SEQ ID NO:2, SEQ ID NO:4, and SEQ ID NO:6.

In another aspect, the present invention provides a modified annexin having an N-terminal chelation site to which is complexed a radionuclide. Suitable radionuclides include $^{64}$Cu, $^{67}$CU, $^{67}$Ga, $^{68}$Ga, $^{186}$Re, $^{188}$Re, $^{99m}$Tc, $^{94}$Tc, $^{95}$Ru, $^{100}$Pd, $^{109}$Pd, $^{212}$Bi, $^{212}$Pb, and $^{111}$In. In a preferred embodiment, the radionuclide complexed to the modified annexins is $^{99m}$Tc. A method for forming representative modified annexins chelated with technetium is described in Example 3. The radiochemical yield and radiochemical purity of the modified annexins of the present invention complexed with technetium is also provided in Example 3.

As summarized in Table 2, the radiochemical yield, defined as the percent yield of the radiolabeled protein based on the radionuclide, for the modified annexins (annexin V-116, -117, and -118) was high (i.e., 79.3, 71.0, and 94.3 percent, respectively) and comparable to the yield for the annexin-chelate conjugate (i.e., $^{99m}$Tc HYNIC-annexin V, 97.0 percent) demonstrating that the modified annexins effectively chelate technetium. Annexin V showed only insignificant nonspecific technetium binding (3.9 percent).

The mean radiochemical yield for labeling annexin V with another exogenous organic chelator ($N_2S_2$-TFP) has been reported to be 48 percent. Stratton et al., *Circulation*, 92:3113–3121, 1995. The radiochemical yields provided by the modified annexins of the present invention are significantly greater than for annexin chelator conjugates.

The radiochemical purity of the technetium labeled annexins was determined after gel filtration and indicated that the modified annexins had high purity (88.3, 89.3, and 98.0 percent, respectively) comparable to the annexin-chelate conjugate (99.0 percent).

The annexin-chelate conjugate used in the comparison was a hydrazinonicotinamide (HYNIC) conjugate. The conjugate and its corresponding technetium complex can be prepared by the methods described in Abrams et al., *J. Nucl. Med.*, 31:2022–2028, 1990 and Blankenberg et al., *Proc. Natl. Acad. Sci. U.S.A.*, 95:6349–6354, 1998. Briefly, the radiolabeled annexin conjugate is prepared in two steps: (1) reaction of annexin with succimidyl 6-HYNIC to provide HYNIC-derivatized annexin; and (2) incubation of the derivatized annexin with $^{99m}$Tc-glucoheptanoate followed by purification by gel filtration to provide the radiolabeled protein. The conjugation method noted above using a chelate-derivatized protein conjugate is characteristic for incorporating radionuclides into proteins.

Among the modified annexins of the invention, the highest radiochemical yield and radiochemical purity was obtained for annexin V-118, which includes the amino acid extension Cys-Gly-Cys. In contrast to the other modified annexins, annexin V-118 includes two cysteine residues in the amino acid extension rather than the single cysteine residue in the extensions of annexin V-116 and -117, which include the sequences Cys-Gly-Gly and Gly-Gly-Cys, respectively. Accordingly, the modified annexin including the sequence Cys-Gly-Cys can be characterized as an $N_2S_2$ peptide chelate and the other modified annexins including the sequences Cys-Gly-Gly and Gly-Gly-Cys, respectively, can be characterized as $N_3S$ peptide chelates. The term "$N_xS_y$," refers to the chelates coordination to the radionuclide. Conventional $N_xS_y$ chelating compounds are described in international patent application Serial No. PCT/US97/12977, expressly incorporated herein by reference. In the present invention, the modified annexin including the $N_2S_2$ peptide chelate (i.e., the amino acid extension Cys-Gly-Cys) provides the highest radiochemical yield and purity.

The bioactivity of the modified annexins of the present invention is described in Example 4. In Example 4, the affinity of the modified annexins for cell membranes was determined by their ability to compete with a fluorescein-labeled annexin V for binding to erythrocytes having exposed phosphatidylserine.

As summarized in Table 3, in the competitive binding assay, the modified annexins of the present invention exhibited a binding slightly diminished compared to the fluorescein annexin V derivative ($IC_{50}$=9.3, 10.3, and 10.1 compared to 6.8 for wild-type annexin V). However, the binding of the modified annexins was substantially equivalent to the annexin chelate conjugate ($IC_{50}$=10.1).

The binding of the radiolabeled-modified annexins to erythrocytes was also determined by measuring the percent radioactivity bound to the cells after incubation with the modified annexins. The results summarized in Table 4, show that the binding of the modified annexins was comparable or greater than that for the annexin-chelate conjugate.

The results demonstrate that the modified annexins of the present invention can effectively chelate a radionuclide and retain annexin bioactivity. The results demonstrate that the modified annexins of the invention can be readily prepared in high radiochemical yield and with high radiochemical purity, and are as effective as a conventional annexin-chelate conjugate with regard to their binding properties.

In contrast to conventional annexin-chelate conjugates, the modified annexins of the invention offer the simplicity of manufacture as an advantage. While conventional chelate conjugates require multiple chemical and purification steps, the modified annexins require only incubation with the radionuclide to provide the diagnostic reagent. Thus, the present invention simply provides a clinically useful imaging reagent. Furthermore, because conventional conjugation chemistries ordinarily rely on conjugation through a protein's lysine residues, the number and location of the conjugated moiety is highly variable, and it is not uncommon for conjugation to occur at or near the site of biological activity thereby inhibiting the conjugate's biological activity. In contrast to conventional conjugation chemistries that provide a distribution of conjugation products, the present invention provides a modified protein having a single chelation site remote from the site of biological activity.

In another aspect of the present invention, methods for using the modified annexins to image vascular thrombi and apoptosis are provided.

Annexin derivatives have been utilized to image vascular thrombi. The highly selective uptake of radiolabeled annexin V on left atrial thrombi in a porcine model has established the feasibility of detecting left atrial thrombi in vivo using gamma camera imaging of the radiolabeled annexin. Stratton et al., *Circulation*, 92:3113–3121, 1995, expressly incorporated herein by reference. In the method, intracardiac thrombi were imaged using a $^{99m}$Tc—$N_2S_2$ complex that was preformed and then covalently conjugated to annexin V. The technetium complex was prepared as described in Kasina et al., *J. Nucl. Med.*, 32:1445–1451, 1991. To image the thrombi, the radiolabeled annexin was injected into a peripheral vein of the animal after anesthetization and left atrial thrombi formation. Gamma camera imaging provided planar and tomographic images for a period of time after injection. Autoradiographic results were obtained for select tissue sections after killing the animal. The imaging results demonstrated that left atrial appendage to blood ratios were significantly higher by both planar and tomographic methods in animals with radiolabel annexin injection and left atrial thrombi than in controls without thrombi. All thrombi were either positively or equivocally positive and the quantitative visual analysis scores and the quantitative thrombus to blood ratios were highest at 2 to 3 hours after injection.

In another aspect, the present invention provides a method for imaging vascular thrombi. The method detects the presence and location of vascular thrombi. In the method, an effective amount of a radiolabeled modified annexin of the invention is administered to a warm-blooded animal and images recorded. Preferably the images are obtained using a gamma camera and are recorded. As used herein, the term "effective amount" refers to an amount of radiolabeled modified annexin sufficient to image vascular thrombi in vivo. For the purposes of this invention, an effective amount of radiolabeled modified annexin is about 10 micrograms annexin per kilogram of body weight, administered intravenously.

A radiolabeled annexin derivative has also been used to image apoptosis. Localization of $^{99m}$Tc HYNIC-annexin V at sites of apoptotic cell death in vivo has been reported. For example, in vivo localization of $^{99m}$Tc HYNIC-annexin V was observed in fuminant hepatic apoptosis induced by anti-Fas antibody rejection in BALB/c mice; acute rejection in ACI rats with transplanted heterotopic PVG cardiac allografts; and cyclophosphamide treatment of transplanted 38C13 murine B cell lymphomas. Blankenberg et al., *J. Nucl. Med.* 40:184–191, 1999; and Blankenberg et al., *Proc. Natl. Acad. Sci. U.S.A.* 95:6349–6354, 1998, each expressly incorporated herein by reference. External radionuclide imaging showed a two- to sixfold increase in the uptake of radiolabeled annexin at sites of apoptosis in all three animal models. These results demonstrate that radiolabeled annexin V can be used in vivo as a noninvasive means to detect and serially image tissues and organs undergoing programmed cell death.

Radiolabeled annexin has also been used for in vivo imaging of apoptosis during cardiac allograft rejection. Vriens et al., *The Journal of Thoracic and Cardiovascular Surgery*, 116:844–853, 1998, expressly incorporated herein by reference. Untreated rats served as recipients of allogenic PVG rat or syngeneic ACI rat cardiac grafts. Recipient animals underwent $^{99m}$Tc HYNIC-annexin V imaging daily for seven days and region of interest analysis was used to quantify the uptake of annexin radiolabel. One animal group was treated with cyclosporin commencing on day four after transplantation. Untreated allografts showed signs of rejection four days after transplantation. Nuclear imaging indicated a significant uptake of the radiolabeled annexin in rejecting allogenic grafts than in syngeneic grafts after transplantation. A correlation between acute rejection and radiolabel uptake was observed and, after treatment with cyclosporin, no apoptotic nuclei could be identified in the allografts and radiolabel annexin uptake decreased to baseline. The results demonstrate that radiolabeled annexin V can be used in vivo as a noninvasive means to detect and monitor cardiac allograft rejection.

In a further aspect, the present invention also provides a method for imaging apoptosis. The method detects the presence and location of apoptotic cells. In the method, an effective amount of a radiolabeled modified annexin of the invention is administered to a warm-blooded animal and nuclear images obtained. Preferably the images are obtained using a gamma camera. As used herein, the term "effective amount" refers to an amount of radiolabeled modified annexin sufficient to image apoptotic cells in vivo. For the purposes of this invention, an effective amount of radiolabeled modified annexin is about 10 micrograms annexin per kilogram of body weight, administered intravenously. The method can be useful for imaging apoptosis associated with response to a chemotherapeutic agent.

The present invention provides amino acid sequences that are effective as chelation sites for a radionuclide. As noted above, the amino acid sequence includes the sequence $X_1$-Gly-$X_2$, where $X_1$ and $X_2$ are selected from Gly and Cys, and where at least of $X_1$ or $X_2$ is Cys. While the chelation site can be effectively incorporated into annexin to provide useful imaging agents as described above, it will be appreciated that the peptide chelates (i.e., the chelating amino acid sequences) can be incorporated into other molecules, including peptides and proteins, to provide modified molecules having chelation sites. The amino acid sequence can be incorporated into a molecule by chemical means. Alternatively, for peptides and proteins, the amino acid sequence is preferably incorporated by recombinant methods to provide a peptide or protein having an endogenous chelation site. The chelation site is preferably incorporated into a peptide or protein at either the C- or N-terminus, preferably distant from the peptide's or protein's binding site.

The following examples are provided for the purposes of illustration and not limitation.

EXAMPLES

Example 1

Construction and Verification of Plasmids

Four plasmids were constructed to express mutant forms of annexin V in *E. coli* under control of the phage T7 promoter. The parent expression vector was pET12a, available from Novagen Corporation (Madison, Wis.).

a. Construction of Expression Vector pJ115, Encoding Annexin V-115 With Cys-316->Ser Mutation (Position 316 Refers to Wild-Type Annexin V).

Figure 2:
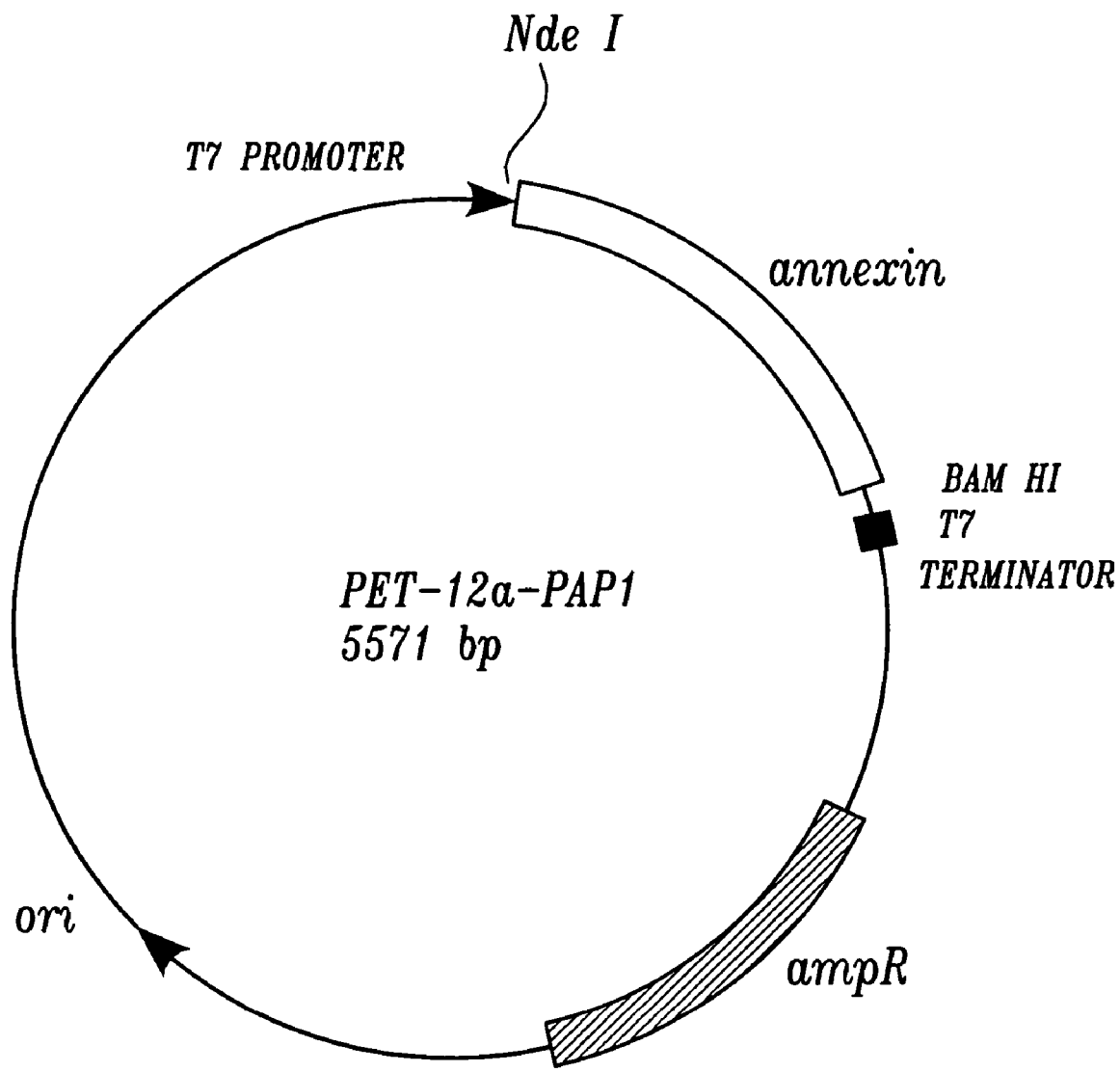
FIG. 2 schematically represents pET-12a-PAP1.

A 232-bp BstBI-BamHI restriction fragment was first isolated from plasmid pANXVC-S-N6, also known as pJ110, which encodes a modified annexin V with the Cys-316->Ser mutation. Tanaka K., et al., "Preparation and characterization of a disulfide-linked bioconjugate of annexin V with the B-chain of urokinase: an improved fibrinolytic agent targeted to phospholipid-containing thrombi," *Biochemistry*, 1996; 35:922–9. The same restriction fragment was then removed from plasmid pET12a-PAP1 (FIG. 2) (Wood, B. L., et al., "Increased erythrocyte phosphatidylserine exposure in sickle cell disease: flow-cytometric measurement and clinical associations," *Blood*, 1996; 88:1873–80), which encodes wild-type annexin V, and the mutated fragment was ligated into the resulting vector to form plasmid pJ115. This plasmid was subjected to DNA sequence analysis to verify that the intended mutation had been correctly introduced.

b. Construction of Expression Vectors pJ116, pJ117, and pJ118, Encoding the Mutant Annexin V Molecules Annexin V-116, Annexin V-117, and Annexin V-118.

9

For each vector to be constructed, sense and antisense oligonucleotides (sequences given in the table below) were designed to encode the desired peptide sequence with NdeI restriction sites at both ends. Equimolar amounts of sense and antisense oligonucleotide were then phosphorylated and annealed to form a double-stranded cassette with NdeI-compatible single-stranded ends. The double-stranded oligonucleotide (3.8 ng) was then ligated with plasmid pJ115 (0.42 µg) that had been previously digested with NdeI and dephosphorylated. The ligation mixture was then transformed into E. coli strain DH5alpha. Plasmid DNA was prepared from ampicillin-resistant colonies and screened by PCR for the presence of the desired insert. DNA sequence analysis was then performed on positive clones to verify that the desired insertion was present.

TABLE 1

Sense and Antisense Oligonucleotides for Construction of Pj116, Pj117 and Pj118

| Name | Vector | Sequence (5' to 3') |
|---|---|---|
| JT-289 | pJ116 | TATGGCATGTGGCGGTGGCCA (SEQ ID NO:7) |
| JT-290 | pJ116 | TATGGCCACCGCCACATGCCA (SEQ ID NO:8) |
| JT-295 | pJ117 | TATGGCAGGTGGCTGTGGCCA (SEQ ID NO:9) |
| JT-296 | pJ117 | TATGGCCACAGCCACCTGCCA (SEQ ID NO:10) |
| JT-297 | pJ118 | TATGGCATGTGGCTGCGGTCA (SEQ ID NO:11) |
| JT-298 | pJ118 | TATGACCGCAGCCACATGCCA (SEQ ID NO:12) |

Example 2

Expression and Purification of Proteins

Plasmids pJ116, pJ117, and pJ118 were each transformed into E. coli strain BL21(DE3) for cytoplasmic expression. Each resulting clone was grown overnight to saturation at 37° C. with shaking in Terrific Broth containing carbenicillin (50 µg/ml). The cells were then separated from culture medium by centrifugation for 10 min at 2560×g and washed in ice-cold buffer (50 mmol/L Tris HCl, 150 mmol/L NaCl pH 8.0). Bacteria were then disrupted by sonication in ice-cold 50 mmol/L Tris HCl pH 7.2, 10 mmol/L CaCl$_2$, 1 mmol/L β-mercaptoethanol, and then centrifuged for 20 min at 22,530×g. The supernatant was discarded and the annexin V bound to bacterial membranes was released by resuspending the pellet in 50 mmol/L Tris HCl pH 7.2, 20 mmol/L EDTA, 1 mmol/L β-mercaptoethanol. Bacterial membranes were then removed by centrifugation for 20 min at 22,530×g and the supernatant containing the annexin V was dialyzed against 20 mmol/L Tris HCl pH 8.0, 1 mmol/L β-mercaptoethanol. The dialysand then was applied to a Mono Q column (Pharmacia, Piscataway, N.J.) and eluted with a gradient of 0 to 1 mol/L NaCl in the same buffer. The annexin V mutants all eluted at approximately 0.22 mol/L NaCl. The purified protein was concentrated by ultrafiltration to a concentration of approximately 5 mg/ml, dialyzed against 20 mmol/L HEPES pH 7.4, 100 mmol/L NaCl, and stored in aliquots at −70° C. The final yield was approximately 10 mg/L of culture, with a purity of ~98% as judged by SDS-polyacrylamide gel electrophoresis.

10

Example 3

Technetium Labeling of Representative Modified Annexins

A representative procedure for technetium labeling of the modified annexins prepared as described above is as generally described in Larsen et al., "[$^{99m}$Tc]Tricine: A useful precursor complex for the radiolabeling of hydrazinonicotinate protein conjugates," *Bioconjugate Chem.*, 6:635–638, 1995, and Blankenberg et al., "In vivo detection and imaging of phosphatidylserine expression during programmed cell death," *Proc. Natl. Acad. Sci. U.S.A.*, 95:6349–6354, 1998, both expressly incorporated herein by reference.

Briefly, annexin is first reduced with dithiothreitol and then labeled with technetium.

Dithiothreitol Reduction:

1. Add dithiothreitol (100 mM in water) to annexin stock solution (3–8 mg/ml in 20 mM HEPES-Na pH7.4, 100 mM NaCl) to 1 mM final concentration. For example, to 600 µg of annexin in 200 µg add 2 µl of 100 mM dithiothreitol.
2. Incubate 15 min at 37° C.
3. Purify by gel filtration on Sephadex G-25 column previously equilibrated with deoxygenated 20 mM sodium citrate pH 5.2, 100 mM NaCl. Store at −70° C. For example:
   a) Equilibrate Pharmacia NAP-5 column with three top column volumes of deoxygenated citrate buffer (20 mM sodium citrate pH 5.2, 100 mM NaCl. Deoxygenate by bubbling with argon.
   b) Add 200 µl of sample to column. Let run in and do not collect.
   c) Add 500 µl deoxygenated citrate buffer. Let run in and do not collect.
   d) Add 600 µl deoxygenated citrate buffer. Let run in and collect. Should now have 600 µg in 600 µl or 50 µg in 50 µl.
   e) Store in aliquots of 500 to 100 µg at −70° C.

Technetium Labeling:

1. Thaw out 100 µg of reduced annexin V-SH (aliquot with 50 to 100 µg in 50 µl of 20 mM sodium citrate pH 5.2, 100 mm NaCl).
2. Reconstitute Tin/Tricine reagent (aliquot lyophilized from 1 ml of 20 mM tricine, 80 µg/mL SnCl$_2$.2H$_2$O, pH 7.1) with 1 ml of distilled water.
3. Add 0.9% NaCl to annexin as necessary to bring final reaction volume to 200 µl.
4. Add 100 µl Tin/Tricine reagent to annexin and mix gently.
5. Add 500 µCi $^{99m}$TcO$_4$ (99mTcO4 in 0.9% NaCl) to annexin and mix gently.
6. Incubate 15 min at room temperature.
7. Determine percent incorporation of technetium into protein by ITLC in PBS (percent radiochemical yield).
8. Purify by gel filtration on Sephadex G25 column in PBS (phosphate-buffered saline). For example:
   a) Equilibrate NAP-5 column (Sephadex G-25, Pharmacia #17-0853-01) with PBS, three top column volumes.
   b) Add 200 µl of sample to column. Let run in and do not collect.
   c) Add 500 µl PBS. Let run in and do not collect.
   d) Add 400 µl PBS. Let run in and collect.
9. Determine percent of technetium bound to annexin by ITLC (instant thin-layer chromatography) in PBS (percent radiochemical purity).

The results of labeling annexin V, modified annexins of the invention (identified as annexins V-116, V-117, and V-118), and an annexin chelate conjugate (HYNIC-annexin V) are summarized in Table 2.

TABLE 2

Annexin Labeling With
Technetium: Radiochemical Yield and Purity

| Protein | % Radiochemical Yield | % Radiochemical Purity |
|---|---|---|
| Annexin V | 3.9 ± 1.6 | Not applicable |
| Annexin V-116 | 79.3 ± 1.2 | 88.3 ± 3.2 |
| Annexin V-117 | 71.0 ± 7.9 | 89.3 ± 4.7 |
| Annexin V-118 | 94.3 ± 0.6 | 98.0 ± 0.0 |
| HYNIC-annexin V | 97.0% | 99.0% |

In the table, results given as mean±SD with n=2 for annexin V, n=3 for mutants 116, 117, and 118, and n=1 for HYNIC-annexin V. Radiochemical purity (%) was determined after purification by gel filtration.

Example 4

Bioactivity of Representative Modified Annexins

The bioactivity of the modified annexins of the invention was determined by a competitive binding assay and by measuring binding to erthyrocytes having exposed phosphatidylserine. The bioactivity of the modified annexins was compared to the activities of native annexin V and an annexin chelate conjugate, HYNIC-annexin V.

Competitive Binding Assay. The affinity of the annexins for cell membranes was determined by their ability to compete with fluorescein-labeled annexin V for binding to erythrocytes having exposed phosphatidylserine. Erythrocytes were obtained commercially (4 Cplus Normal Control, Beckman-Coulter Corp., Hialeah, Fla.). The annexins were added at various concentrations to 1 ml of a solution containing 5 nM fluorescein-annexin V and $8.3 \times 10^6$ erythrocytes in a buffer consisting of 10 mM HEPES-NA pH 7.4, 136 mM NaCl, 2.7 mM KCl, 5 mM glucose, 1 mg/ml BSA (buffer HNKGB) plus 2.5 mM $CaCl_2$. Samples were incubated for 15 min at room temperature. The cells were then centrifuged, the supernatant removed, and the fluorescein-annexin V bound to the pelleted cells was released by resuspension in 950 μl HNKGB buffer containing 5 mM EDTA. The sample was then centrifuged again, the supernatant removed, and the concentration of fluorescein-annexin V in the supernatant determined by fluorometry. The results of this assay are summarized in Table 3 and presented as the concentration of competitor protein that inhibits 50% of the binding of fluorescein-annexin V, abbreviated $IC_{50}$.

TABLE 3

Annexin Bioactivity by Competition Binding Assay

| Protein | $IC_{50}$ (nmol/L) |
|---|---|
| Annexin V | 6.8 ± 0.7 |
| Annexin V-116 | 9.3 ± 0.4 |
| Annexin V-117 | 10.3 ± 2.5 |
| Annexin V-118 | 10.1 ± 2.8 |
| HYNIC-annexin V | 10.1 ± 2.0 |

In the table, results given as mean±SD with n=9 for annexin V, n=2 for mutants 116, 117, and 118, and n=9 for HYNIC-annexin V.

Erythrocyte Binding Assay. The ability of radiolabeled annexins to bind to cell membranes was determined by measuring the percent radioactivity bound to erythrocytes as follows. Radiolabeled annexins at 10 nmol/L final concentration was added to duplicate tubes containing a final volume of 1 ml of buffer HNKGB plus 2.5 mM $CaCl^2$. One tube then received $4.2 \times 10^8$ erythrocytes. After a 15-min incubation at room temperature, both tubes were centrifuged for three min at 8,320×g. Radioactivity was then measured in 800 μl of the supernatants. The percentage of radioactivity bound to the cells was calculated using the following equation: 100(1−(supernatant counts in presence of cells)/ (supernatant counts in absence of cells)).

TABLE 4

Annexin Bioactivity by Binding
of Radiolabeled Proteins to Erythrocytes

| Protein | % Radioactivity Bound to Erythrocytes |
|---|---|
| Annexin V-116 | 80.3 ± 2.9 |
| Annexin V-117 | 84.3 ± 2.5 |
| Annexin V-118 | 86.3 ± 2.1 |
| HYNIC-annexin V | 83.9 ± 2.5 |

Results given as mean±SD with n=3 for mutants 116, 117, and 118, n=7 for HYNIC-annexin V.

Example 5

Hybridization of Nucleic Acid Molecules Encoding Modified Annexins to Other Nucleic Acid Sequences The nucleic acid molecules of the present invention are capable of hybridizing to the nucleic acid sequences set forth in SEQ ID NO:1, SEQ ID NO:3, or SEQ ID NO:5, or to the complementary sequence of the nucleic acid sequences set forth in SEQ ID NO:1, SEQ ID NO:3, or SEQ ID NO:5, under the following stringent hybridization conditions: incubation in 5×SSC at 65° C. for 16 hours, followed by washing under the following conditions: two washes in 2×SSC at 18° C. to 25° C. for twenty minutes per wash; preferably, two washes in 2×SSC at 18° C. to 25° C. for twenty minutes per wash, followed by one wash in 0.5×SSC at 55° C. for thirty minutes; most preferably, two washes in 2×SSC at 18° C. to 25° C. for fifteen minutes per wash, followed by two washes in 0.2×SSC at 65° C. for twenty minutes per wash. The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

The ability of the nucleic acid molecules of the present invention to hybridize to the nucleic acid sequences set forth in SEQ ID NO:1, SEQ ID NO:3, or SEQ ID NO:5, or to the complementary sequence of the nucleic acid sequences set forth in SEQ ID NO:1, SEQ ID NO:3, or SEQ ID NO:5 can be determined utilizing the technique of hybridizing radiolabelled nucleic acid probes to nucleic acids immobilized on nitrocellulose filters or nylon membranes as set forth, for example, at pages 9.52 to 9.55 of Molecular Cloning, A Laboratory Manual (2nd edition), J. Sambrook, E. F. Fritsch and T. Maniatis eds., the cited pages of which are incorporated herein by reference.

In addition to the nucleic acid sequences set forth in SEQ ID NO:1, SEQ ID NO:3, and SEQ ID NO:5, examples of representative nucleic acid sequences that encode the modified annexins of the invention and which hybridize to the complementary sequence of the nucleic acid sequences disclosed in SEQ ID NO:1, SEQ ID NO:3, and SEQ ID NO:5 can be computer generated by utilizing the degeneracy of the genetic code. Each of the representative nucleic acid sequences has a different sequence, but each encodes a modified annexin of the invention.

While the preferred embodiment of the invention has been illustrated and described, it will be appreciated that various changes can be made therein without departing from the spirit and scope of the invention.

---

The embodiments of the invention in which an exclusive property or privilege is claimed are defined as follows:

1. A method for imaging apoptosis comprising
   administering to a warm-blooded animal an effective amount a modified annexin having an N-terminal chelation site, wherein the chelation site comprises an amino acid extension comprising an amino acid sequence $X_1$-Gly-$X_2$, wherein $X_1$ and $X_2$ are selected from Gly and Cys, wherein at least one of $X_1$ or $X_2$ is Cys, and wherein a radionuclide is complexed to the chelation site; and
   obtaining nuclear images of the animal to determine the presence and location of apoptotic cells.

2. The method of claim 1, wherein the amino acid extension comprises the amino acid sequence Gly-Gly-Cys.

3. The method of claim 1, wherein the amino acid extension comprises the amino acid sequence Cys-Gly-Gly.

4. The method of claim 1, wherein the amino acid extension comprises the amino acid sequence Cys-Gly-Cys.

5. The method of claim 1, wherein the apoptosis is associated with rejection as a result of transplantation.

6. The method of claim 1, wherein the apoptosis is associated with response to a chemotherapeutic agent.

* * * * *

UNITED STATES PATENT AND TRADEMARK OFFICE
CERTIFICATE OF CORRECTION

PATENT NO. : 7,204,972 B2　　　　　　　　　　　　　　　　　　　　　　　Page 1 of 1
APPLICATION NO. : 11/012708
DATED : April 17, 2007
INVENTOR(S) : J.F. Tait et al.

It is certified that error appears in the above-identified patent and that said Letters Patent is hereby corrected as shown below:

| COLUMN | LINE | ERROR |
|---|---|---|
| 27 (Claim 1, | 19 line 1) | after "comprising" insert --:-- |
| 27 (Claim 1, | 21 line 3) | "amount a" should read --amount of a-- |

Signed and Sealed this

Fourteenth Day of August, 2007

JON W. DUDAS
*Director of the United States Patent and Trademark Office*